: US 9,125,810 B2

(12) United States Patent
Gyakushi et al.

(10) Patent No.: US 9,125,810 B2
(45) Date of Patent: *Sep. 8, 2015

(54) ALGINIC ACID-CONTAINING AQUEOUS COMPOSITION, DENTAL ALGINATE IMPRESSION MATERIAL, AND BASE MATERIAL FOR DENTAL ALGINATE IMPRESSION MATERIAL

(75) Inventors: Hidetoshi Gyakushi, Tokyo (JP); Koji Matsushige, Tokyo (JP); Yuko Nagasawa, Tokyo (JP)

(73) Assignee: TOKUYAMA DENTAL CORPORATION (JP)

( * ) Notice: Subject to any disclaimer, the term of this patent is extended or adjusted under 35 U.S.C. 154(b) by 39 days.

This patent is subject to a terminal disclaimer.

(21) Appl. No.: 13/641,197

(22) PCT Filed: Apr. 20, 2011

(86) PCT No.: PCT/JP2011/059703
§ 371 (c)(1),
(2), (4) Date: Oct. 15, 2012

(87) PCT Pub. No.: WO2011/132699
PCT Pub. Date: Oct. 27, 2011

(65) Prior Publication Data
US 2013/0032058 A1    Feb. 7, 2013

(30) Foreign Application Priority Data

Apr. 22, 2010 (JP) .................................. 2010-111495
Nov. 15, 2010 (JP) .................................. 2010-255085

(51) Int. Cl.
*A61K 6/10*        (2006.01)
*A61K 6/00*        (2006.01)

(52) U.S. Cl.
CPC ............. *A61K 6/0088* (2013.01); *A61K 6/0047* (2013.01); *A61K 6/10* (2013.01)

(58) Field of Classification Search
USPC ................................................. 106/35, 205.7
See application file for complete search history.

(56) References Cited

U.S. PATENT DOCUMENTS

| 4,959,220 A | 9/1990 | Yamamoto |
| 2005/0032720 A1 | 2/2005 | Wingrove |
| 2005/0180930 A1 * | 8/2005 | Abiru et al. ............. 424/58 |
| 2006/0213396 A1 | 9/2006 | Kamohara |
| 2010/0120941 A1 | 5/2010 | Oguri et al. |

FOREIGN PATENT DOCUMENTS

| CN | 101605523 B | 9/2012 |
| EP | 0048123 A1 | 3/1982 |
| EP | 1886659 A1 | 2/2008 |
| FR | 1235470 A | 7/1960 |
| JP | 62-265210 A | 11/1987 |
| JP | 5-17315 A | 1/1993 |
| JP | 10-139615 A | 5/1998 |
| JP | 10-139616 A | 5/1998 |
| JP | 11-100323 A | 4/1999 |
| JP | 11-209220 A | 8/1999 |
| JP | 2002-87922 A | 3/2002 |
| JP | 2003-171219 A | 6/2003 |
| JP | 2004-269385 A | 9/2004 |
| JP | 2006-193475 A | 7/2006 |
| JP | 2006-206481 A | 8/2006 |
| JP | 2006-225323 A | 8/2006 |
| JP | 2006-248960 A | 9/2006 |

OTHER PUBLICATIONS

Material Safty Data Sheet for GC Aroma Fine DF III, Jul. 16, 2007.*
International Search Report for International Application No. PCT/JP2011/059703, mailed May 24, 2011, with English translation.
Sakurai, Minoru , et al., "Hydration characteristics of carbohydrates and physiological functions of trehalose," Biophysics, The Biophysical Society of Japan, 1997, vol. 37, pp. 326-330.
Chinese Office Action issued for Chinese Patent Application No. 201180015692.1; Date of Mailing: Sep. 10, 2013; w/English Translation.
European Search Report for the Application No. 11772032.6-1501/2561852, dated Feb. 14, 2014.
Syed K. H. Gulrez et al. (2011), "Hydrogels: Methods of Preparation, Characterization and Applications, Progress in Molecular and Environmental Bioengineering", From Analysis and Modeling to Technology Applications, Prof. Angelo Carpi (Ed.) ISBN: 978-9536-307-268-5, in Tech, available from : http://www.intechopen.com; pp. 117-151.

* cited by examiner

*Primary Examiner* — Carol M Koslow
(74) *Attorney, Agent, or Firm* — Cantor Colburn LLP

(57) ABSTRACT

Provided is an aqueous composition containing alginic acid or a derivative thereof, the composition having a viscosity retained stably over a long period of time. The alginic acid-containing aqueous composition includes alginic acid or a derivative thereof (A), water (B), and a non-reducing sugar (C). Also provided are a dental alginate impression material and a base material for a dental alginate impression material each using the composition, in which the viscosity of the aqueous composition is stably maintained for a long period.

6 Claims, 1 Drawing Sheet

ALGINIC ACID-CONTAINING AQUEOUS COMPOSITION, DENTAL ALGINATE IMPRESSION MATERIAL, AND BASE MATERIAL FOR DENTAL ALGINATE IMPRESSION MATERIAL

CROSS REFERENCE TO RELATED APPLICATIONS

This is a U.S. national stage of application No. PCT/JP2011/059703, filed on 20 Apr. 2011. Priority under 35 U.S.C. §119 (a) and 35 U.S.C. §365(b) is claimed from Japanese Application Nos. 2010-111495, filed 22 Apr. 2010, and 2010-255085, filed 15 Nov. 2010, the disclosure of which are also incorporated herein by reference.

TECHNICAL FIELD

The present invention relates to a dental alginate impression material, and a base material for a dental alginate impression material.

BACKGROUND ART

Alginic acid or a derivative thereof (hereinafter, sometimes collectively referred to as "alginic acid") has property of forming a very viscous and homogeneous solution when dissolved in an aqueous solution, and is used in a product for which such viscous property is demanded in terms of operability and the like, for example, a food such as jam, sauce, or mayonnaise or an ophthalmic composition such as an eye lotion or a contact lens care solution. Further, the alginic acid or the derivative thereof has property of gelling upon contact with a polyvalent metal ion such as a calcium ion, and hence is generally used as a dental impression material, in particular.

However, it is known that such alginic acid exhibits a time-dependent decrease in viscosity in an aqueous solution. Therefore, in an alginic acid aqueous solution or an alginic acid-containing aqueous composition obtained by adding a filler thereto, its viscosity cannot be retained stably over a long period of time, which is a major factor for deterioration in handleability of the composition. In view of the foregoing, in the alginic acid-containing aqueous composition, it has been a big problem to retain the viscosity stably over a long period of time, from the viewpoint of improving storage stability of the composition.

In order to overcome the problem, there have been developed methods of suppressing a decrease in viscosity of an alginic acid-containing aqueous composition by blending an additive in the composition (Patent Literatures 1 to 4). However, all of the methods involve the following problems: there is a limitation on an applicable composition; and the blending of the additive causes a decrease in initial viscosity of the composition, with the result that a desired initial viscosity cannot be obtained.

Meanwhile, a pasty dental alginate impression material blended with an organic hydroxy compound typified by a saccharide has been developed (Patent Literatures 5 and 6). The organic hydroxy compound used in the material is blended in order to improve tooth release property and tray retention property, and one satisfying the following mathematical equation (1) is used.

$$(\text{Molecular weight}) \div (\text{Number of hydroxy groups}) < 40 \quad \text{Equation (1)}$$

The literatures mention, as specific examples of the organic hydroxy compound, saccharides such as glucose, fructose, mannose, and ribose, sugar alcohols such as sorbitol, mannitol, and maltitol, and polyhydric alcohols such as glycerin. All of the sugars mentioned in the literatures belong to reducing sugars. However, the blending with each of those reducing sugars has little effects of suppressing the time-dependent decrease in viscosity in the alginic acid-containing aqueous composition.

CITATION LIST

Patent Literature

[PTL 1] JP 2006-193475 A
[PTL 2] JP 2006-206481 A
[PTL 3] JP 2006-225323 A
[PTL 4] JP 2006-248960 A
[PTL 5] JP 2003-171219 A
[PTL 6] JP 4322025 B2
[PTL 7] JP 2004-269385 A
[PTL 8] JP 10-139615 A
[PTL 9] JP 10-139616 A

Non Patent Literature

[NPL 1] Minoru Sakurai, Yoshio Inoue, "Hydration characteristics of carbohydrates and physiological functions of trehalose," Biophysics, The Biophysical Society of Japan, 1997, Vol. 37, pp. 326-330

SUMMARY OF INVENTION

Technical Problem

Under such background, an object of the present invention is to provide an alginic acid-containing aqueous composition having a viscosity retained stably over a long period of time without causing any decrease in initial viscosity, and a dental alginate impression material and a base material for a dental alginate impression material each using the composition.

Solution to Problem

The inventors of the present invention have made extensive studies in order to achieve the technical object. As a result, the inventors have found that a time-dependent decrease in viscosity of the alginic acid-containing aqueous composition is suppressed by further incorporating a non-reducing sugar into the composition. Thus, the present invention has been completed.

That is, the alginic acid-containing aqueous composition of the present invention includes: alginic acid or a derivative thereof (A); water (B); and a non-reducing sugar (C).

In an alginic acid-containing aqueous composition according to an embodiment of the present invention, it is preferred that the non-reducing sugar (C) include 2 to 10 monosaccharide molecules bonded via a glycosidic bond.

In an alginic acid-containing aqueous composition according to another embodiment of the present invention, it is preferred that the non-reducing sugar (C) include a disaccharide.

In an alginic acid-containing aqueous composition according to another embodiment of the present invention, it is preferred that the content of the non-reducing sugar (C) fall within a range of 1 to 100 parts by weight with respect to 1 part by weight of the alginic acid or the derivative thereof (A).

It is preferred that an alginic acid-containing aqueous composition according to another embodiment of the present invention further include a filler (D), in which the alginic acid-containing aqueous composition be pasty.

A dental alginate impression material of the present invention includes: a base material including an alginic acid-containing aqueous composition including: alginic acid or a derivative thereof (A); water (B); and a non-reducing sugar (C); and a curing material.

In a dental alginate impression material according to an embodiment of the present invention, it is preferred that: the base material be pasty; and the curing material include a pasty curing material including a gelling reaction agent and a poorly water-soluble organic solvent.

In a dental alginate impression material according to another embodiment of the present invention, it is preferred that the content of the non-reducing sugar (C) fall within a range of 1 part by weight to 20 parts by weight with respect to 1 part by mass of the alginic acid or the derivative thereof (A).

In a dental alginate impression material according to another embodiment of the present invention, it is preferred that the non-reducing sugar (C) include 2 to 10 monosaccharide molecules bonded via a glycosidic bond.

In a dental alginate impression material according to another embodiment of the present invention, it is preferred that the non-reducing sugar (C) include a disaccharide.

In a dental alginate impression material according to another embodiment of the present invention, it is preferred that the non-reducing sugar (C) include trehalose.

A base material for a dental alginate impression material of the present invention includes: alginic acid or a derivative thereof (A); water (B); and a non-reducing sugar (C).

In a base material for a dental alginate impression material according to an embodiment of the present invention, it is preferred that a content of the non-reducing sugar (C) fall within a range of 1 part by weight to 20 parts by weight with respect to 1 part by mass of the alginic acid or the derivative thereof (A).

In a base material for a dental alginate impression material according to another embodiment of the present invention, it is preferred that the base material be pasty.

Advantageous Effects of Invention

In the present invention, through the incorporation of the non-reducing sugar into the aqueous composition containing alginic acid or a derivative thereof, it is possible to provide the alginic acid-containing aqueous composition capable of suppressing a time-dependent decrease in viscosity at a high level without causing any decrease in initial viscosity, and the dental alginate impression material and the base material for a dental alginate impression material each using the composition.

Figure 1:
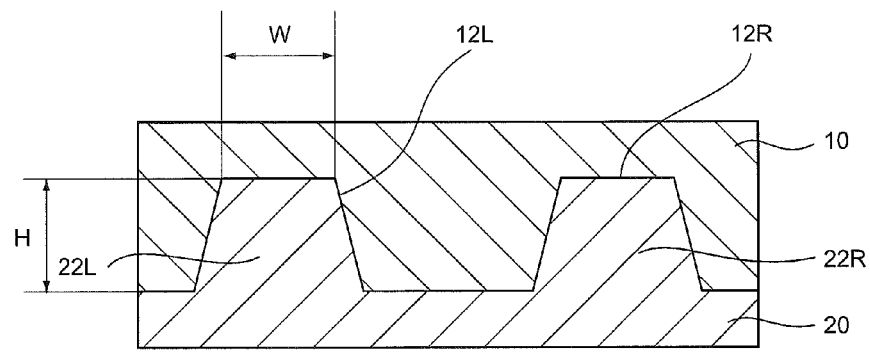
FIG. 1 A schematic view illustrating a pair of molds used in the evaluation of compatible deformation.

DESCRIPTION OF EMBODIMENTS (Alginic Acid-Containing Aqueous Composition)

In an alginic acid-containing aqueous composition according to this embodiment, through the blending of alginic acid or a derivative thereof (alginic acid) with a non-reducing sugar, a decrease in viscosity of the composition is suppressed over a long period of time, and the viscosity is retained stably.

In this case, the alginic acid is a linear polymer consisting of two kinds of blocks (1-4)-linked each other, in which two kinds of blocks are β-D-mannuronic acid and α-L-guluronic acid. Besides, the alginic acid derivative is generally a reaction product reacted at a carboxylic acid part. Examples thereof include an alginic acid salt, an ester derivative of alginic acid, and an ether derivative of alginic acid. Specific examples of the alginic acid salt include: alkali metal alginates such as sodium alginate and potassium alginate; and ammonium alginates such as ammonium alginate and triethanolamine alginate. In addition, an example of the ether derivative of alginic acid is an alkylene glycol alginate such as propylene glycol alginate, and an example of the ester derivative of alginic acid is propylene glycol alginate ether. Of those, an alkali metal alginate is preferred because the water solubility thereof is high, and sodium alginate and potassium alginate are particularly preferred. Sodium alginate is most preferred because a time-dependent decrease in viscosity hardly occurs.

It should be noted that any of a natural product and a synthetic product may be used as the alginic acid or alginic acid derivative. Typical examples of the natural product include Macrocystis in the west coast of the United States, Lessonia in Chile in South America, and Ascophyllum in North Europe. However, the kind and production area of seaweed as a raw material are arbitrary. Further, an extraction method is exemplified by an alkali extraction method and a hot water extraction method and is not particularly limited. Further, a ratio between mannuronic acid and guluronic acid constituting alginic acid (mannuronic acid/guluronic acid ratio, hereinafter, abbreviated as "M/G ratio") is not particularly limited and may be selected from a wide range of ratios including a large M/G ratio and a small M/G ratio. Of those, the ratio is preferably 4.0 or less, more preferably 1.5 or less.

Further, a commercially available product may also be utilized. Examples of the commercially available product include alginic acid, sodium alginate, and potassium alginate supplied from Foodchemifa Company, KIMICA Corporation, and Fuji Chemical Industry Co., Ltd.

The content of the alginic acid in the alginic acid-containing aqueous composition according to this embodiment may be appropriately set depending on its kind, molecular weight, and composition (M/G ratio), the kind of a component coexisting in the alginic acid-containing aqueous composition, and a desired viscosity to be imparted to the alginic acid-containing aqueous composition. The viscosity of the alginic acid-containing aqueous composition greatly depends on the molecular weight of the alginic acid as well as the content of the alginic acid. The molecular weight of the alginic acid is generally adopted from a wide range of 10,000 to 1,000,000 in terms of weight average molecular weight. The weight average molecular weight falls within preferably a range of 20,000 to 300,000 in order to impart predetermined viscous property, which leads to excellent handleability, to the alginic acid-containing aqueous composition. Further, the alginic acid has property of gelling upon contact with a divalent or more cation (polyvalent metal ion) such as a calcium ion. In a composition (specifically, a dental alginate impression material) utilizing such gelling ability of the alginic acid, an alginic acid having a 1-wt % aqueous solution viscosity (23° C.) of 50 mPa·s to 1,000 mPa·s is suitably used.

The water contained in the alginic acid-containing aqueous composition according to this embodiment is not particularly limited, and tap water, ion-exchange water, distilled water, or the like may be used. The content of the water is not particularly limited. However, in a composition utilizing the gelling ability of the alginic acid, the content of the water falls within preferably a range of 1 part by weight to 2,000 parts by weight, more preferably a range of 10 parts by weight to 1,000 parts by weight, with respect to 1 part by weight of the alginic acid.

The alginic acid-containing aqueous composition according to this embodiment has a viscosity retained stably over long period of time through the incorporation of a non-reducing sugar. As the non-reducing sugar to be used in the alginic acid-containing aqueous composition according to this embodiment, any saccharide showing no reducing property is used without any limitation. The reducing property as used herein refers to having property of showing a reducing action on a heavy metal ion such as silver or copper in an alkaline solution. A saccharide having reducing property is detected with a Tollens' reagent, a Benedict's reagent, or a Fehling's reagent utilizing a reducing action on a heavy metal ion, whereas the non-reducing sugar to be used in the alginic acid-containing aqueous composition according to this embodiment is a saccharide which is not detected with any of those reagents. Specific examples of the non-reducing sugar include disaccharides such as trehalose and sucrose and oligosaccharides such as raffinose, melezitose, stachyose, and cyclodextrins.

In the alginic acid-containing aqueous composition according to this embodiment, the reason why the decrease in viscosity is suppressed by blending the alginic acid-containing aqueous composition with the non-reducing sugar is not necessarily clear, but the inventors have estimated the reason as described below. That is, it is considered that, in the alginic acid-containing aqueous solution, a hydrogen bond is formed between molecular chains of alginic acid molecules or in a molecular chain of each of alginic acid molecules, resulting in the aggregation of the alginic acid molecules, and hence the viscosity of the aqueous solution decreases with time. On the other hand, it is guessed that, when the non-reducing sugar is present in the alginic acid-containing aqueous composition, a water molecule and the non-reducing sugar form a molecular assembly, and then the formation of a hydrogen bond, i.e., the aggregation of alginic acid molecules is inhibited by the entering of the molecular assembly between molecular chains of alginic acid molecules or in a molecular chain of each of alginic acid molecules, leading to the suppression of the decrease in viscosity of the aqueous composition.

When a non-reducing sugar having an excessively high molecular weight is used as the non-reducing sugar to be used in the alginic acid-containing aqueous composition according to this embodiment, aggregation occurs through the formation of a hydrogen bond between the alginic acid and the non-reducing sugar, and hence an effect of suppressing the decrease in viscosity of the composition is estimated to lower. Therefore, the non-reducing sugar to be used in the alginic acid-containing aqueous composition according to this embodiment is preferably a non-reducing sugar including 2 to 10 monosaccharide molecules bonded via a glycosidic bond, more preferably a disaccharide. When a general alginic acid-containing aqueous composition is used as a pasty or liquid dental alginate impression material (more specifically, a base material), liquid separation as well as the decrease in viscosity of the composition serves as a factor for the deterioration of the base material. However, trehalose has a particularly high hydration ability among the non-reducing sugars (Non Patent Literature 1) and easily forms a molecular assembly with a water molecule. Therefore, a base material formed of an alginic acid-containing aqueous composition containing trehalose hardly causes liquid separation. Hence, trehalose is particularly suitably used as the non-reducing sugar. It should be noted that sucrose serves as a material for an acid, which causes caries, to be produced by bacteria in the oral cavity, and hence is not suitable in the case where the composition is used as the pasty or liquid dental alginate impression material.

The content of the non-reducing sugar in the alginic acid-containing aqueous composition according to this embodiment is not particularly limited and is preferably 0.05 part by weight or more with respect to 1 part by weight of the alginic acid. When the content of the non-reducing sugar is too small, a decrease in viscosity of the composition may not be sufficiently suppressed. Thus, the content is preferably 1 part by weight or more with respect to 1 part by weight of the alginic acid. The upper limit of the content is the maximum solubility of the alginic acid. However, an excessively high viscosity impairs the handleability. In general, therefore, the content of the non-reducing sugar is preferably 100 parts by weight or less with respect to 1 part by weight of the alginic acid. Further, as for a composition utilizing the gelling ability of the alginic acid, a gelling reaction is inhibited when the content of the non-reducing sugar is too large with respect to the alginic acid. Hence, the content of the non-reducing sugar is suitably 50 parts by weight or less with respect to 1 part by weight of the alginic acid.

When a reducing sugar showing reducing property (e.g., all monosaccharides such as glucose, mannose, and galactose, disaccharides such as maltose, lactose, and cellobiose, and oligosaccharides such as panose, maltotriose, and dextrin) is incorporated into the alginic acid-containing aqueous composition, a time-dependent decrease in viscosity of the composition is promoted. The reason why the decrease in viscosity is promoted by blending the alginic acid-containing aqueous composition with the reducing sugar is not necessarily clear, but the inventors have estimated the reason as described below. That is, it is considered that the reducing sugar also has the viscosity decrease suppressing effect as described above, whereas the reducing property of the reducing sugar promotes a hydrolysis reaction of the alginic acid, i.e., a decrease in molecular weight of the alginic acid. It is guessed that the influence of the decrease in viscosity caused by the decrease in molecular weight of the alginic acid is much larger than the viscosity decrease suppressing effect, with the result that the decrease in viscosity of the composition is promoted. Therefore, in the alginic acid-containing aqueous composition according to this embodiment, a case where such reducing sugar is contained in a small amount in addition to the non-reducing sugar is not eliminated, but the content thereof is particularly preferably suppressed to suitably 1 part by weight or less, more preferably 0.05 part by weight or less, with respect to 1 part by weight of the alginic acid.

The use application of the alginic acid-containing aqueous composition according to this embodiment is not limited as long as the application utilizes time-dependent viscosity stability as the characteristic nature of the composition. The composition may be utilized in various products for each of which viscous property is demanded from the viewpoints of handleability and the like, for example, various fields such as dental materials, pharmaceuticals, quasi drugs, cosmetics, foods, and miscellaneous goods. Specific examples thereof include a composition for a dental alginate impression material, an ophthalmic composition such as eye drops or eyewash, an otological composition such as nasal drops or ear drops, an oral composition such as an oropharyngeal drug or a therapeutic drug for stomatitis, and a skin external composition such as a vulnerary.

(Dental Alginate Impression Material and Base Material Paste for Dental Alginate Impression Material)

However, the alginic acid-containing aqueous composition according to this embodiment is particularly suitably applied to a dental alginate impression material out of the above-mentioned various use applications. In this case, the dental alginate impression material according to this embodiment includes a base material formed of the alginic acid-containing aqueous composition according to this embodiment and a curing material.

In this case, a general dental alginate impression material is an impression material containing as components an alginic acid and a gelling reaction agent such as a polyvalent metal salt, and is mainly used for taking an impression of teeth during the treatment and restoration of the teeth. The dental alginate impression material has such features that impression accuracy is good, a minute portion can be reproduced, and an impression operation is easy, for example, and thus is widely used as a dental impression material. In general, two kinds of dental alginate impression materials, i.e., dental alginate impression materials of a powder type and a paste type are widely utilized. Any of the types is used for taking an impression based on the phenomenon that an alginic acid forms a gel, i.e., a cured product having elasticity, through its reaction with a gelling reaction agent such as a polyvalent metal salt in the presence of water. In the case of the pasty impression material, a pasty base material (base material paste) obtained by kneading an alginic acid with water is prepared in advance, and mixed with a pasty curing material (curing material paste) containing as a main component a gelling reaction agent such as a polyvalent metal salt such as calcium sulfate before use.

When the alginic acid-containing aqueous composition according to this embodiment is used in the dental alginate impression material, the alginic acid-containing aqueous composition according to this embodiment is used as a base material constituting the dental alginate impression material. The base material is preferably made pasty by appropriately selecting the concentration and kind of each component to be blended. However the base material may be a liquid having a lower viscosity than the paste. Further, it is suitable to blend a filler in order to prepare a pasty base material.

In this case, a curing material to be used in combination with the base material is a material containing at least a gelling reaction agent, and a pasty material containing a gelling reaction agent and a poorly water-soluble organic solvent (curing material paste) is generally used. That is, a dental alginate impression material (hereinafter, sometimes abbreviated as "alginate impression material") according to this embodiment includes a base material paste including the alginic acid-containing aqueous composition according to this embodiment and a curing material. In this case, a curing material containing a gelling reaction agent and a poorly water-soluble organic solvent (curing material paste) is generally used as the curing material.

In this case, work for taking an impression using a paste type alginate impression material is carried out according to the following procedures. First, a product obtained by kneading constituents of the alginate impression material is mounted on an impression tray made into a similar shape to that of arrangement of teeth. Next, the tray on which the impression material is mounted is pressed against the teeth so that the tray covers the teeth in the oral cavity. Then, after the alginate impression material has been cured, an integrated product of the alginate impression material and the tray is removed from the teeth and taken out from the oral cavity.

A cured alginate impression material (cured product) contains a large amount of water. Hence, when the cured product is left to stand in ambient air after impression taking, moisture evaporates from the cured product, with the result that the shape of the cured product gradually deforms. In addition, such deformation causes a decrease in impression accuracy. Therefore, in the practice of dental therapy, in order to prevent the evaporation of water from the cured product, molding gypsum is injected to the cured product immediately after impression taking to produce a gypsum model, or the cured product is placed in a moist box maintained at a humidity of 80% or more.

Meanwhile, various alginate impression materials have been proposed as the alginate impression material. For example, the applicants of the present invention have proposed an alginate impression material containing an organic hydroxy compound, in which a value obtained by dividing a molecular weight by the number of hydroxyl groups in a molecule is less than 40 and the number of hydroxy groups per molecule is 3 or more, for the purposes of, for example, improving impression material properties (Patent Literatures 6 and 7). Further, there have been proposed alginate impression materials blended with a sugar alcohol such as xylite, a sucrose fatty acid ester, and the like in order to prevent the evaporation of moisture from the cured product (Patent Literatures 8 and 9).

However, such work that molding gypsum is injected to the cured product immediately after impression taking to produce a gypsum model needs to be carried out during consultation hours for a patient concurrently with dental therapy for the patient. Therefore, a very large work burden is imposed on a dentist or a dental hygienist. Further, the method involving placing the cured product in a moist box maintained at a humidity of 80% or more to prevent the evaporation of water from the cured product also does not provide any radical solution to the problem, because the method allows a period of time for which the cured product can be left to stand to be prolonged only slightly.

Further, in each of the alginate impression materials described in Patent Literatures 8 and 9, it is expected that a decrease in impression accuracy can be suppressed by utilizing a moist box even in the case of using the cured product left to stand for about several hours. However, when the fact that impression taking is carried out for a number of patients per day is taken into consideration, a dentist or a dental hygienist needs to carry out daily such work that numerous gypsum models are produced through the use of numerous cured products produced on that particular day, after consultation hours for the patients. Such work imposes a tremendous burden on the dentist or dental hygienist.

When the above-mentioned circumstances are taken into consideration, the alginate impression material is demanded to have such characteristics that the moisture retaining property is excellent, and the impression accuracy hardly decreases even when the cured product is left to stand for a longer period of time after impression taking. In order to satisfy the above-mentioned characteristics, it is particularly preferred that the base material paste to be used in the alginate impression material according to this embodiment, that is, the alginic acid-containing aqueous composition according to this embodiment contain a non-reducing sugar within a range of 1 part by weight to 20 parts by weight with respect to 1 part by weight of the alginic acid.

When an impression is taken through the use of the alginate impression material, the cured product has excellent moisture retaining property, and hence the evaporation of moisture from the cured product is suppressed to a large extent. Therefore, even when the cured product is left to stand for a long period of time, the impression accuracy hardly decreases. Hence, when the cured product is placed and stored in a moist box maintained at a humidity of 80% or more, a decrease in impression accuracy can be satisfactorily suppressed even after the lapse of 1 day or more from impression taking. In this case, it is extremely easy to achieve an additional improvement in work efficiency by producing gypsum models all at once, for example, every 2 or 3 days to several days, or to send cured products to a dental technician and request the dental technician to act as a proxy in producing gypsum models. In addition, a cured product having a very smooth surface is obtained as compared to a case where an impression is taken through the use of a conventional alginate impression material, and tends to be maintained in this state even when left to stand for a long period of time. Thus, it is also easy to achieve higher impression accuracy than ever before.

The reason why the above-mentioned effects are obtained is not clear, but the inventors have estimated that the effects are obtained by virtue of the use of the non-reducing sugar as described below. First, the non-reducing sugar has high affinity with a water molecule (hydration ability). Therefore, it is considered that, when a base material and a curing material are kneaded together in order to take an impression through the use of the alginate impression material according to this embodiment, the non-reducing sugar forms a molecular assembly together with a water molecule. Then, it is considered that a hydrogen bond is formed between each of alginic acid molecules having a hydroxy group, an ether bond, and the like and the molecular assembly by the entering of the molecular assembly between molecular chains of the alginic acid molecules and/or in a molecular chain of each of the alginic acid molecules, resulting in the strong fixation of the water molecule. That is, it is considered that the water molecule is strongly fixed in a cured product containing a large amount of moisture, leading to the suppression of the evaporation of moisture of the cured product. Then, as a result, the cured product is estimated to have excellent moisture retaining property.

It should be noted that, in order to obtain the above-mentioned effects, the blending amount of the non-reducing sugar needs to fall within a range of 1 part by weight to 20 parts by weight, and falls within preferably a range of 2 parts by weight to 15 parts by weight, more preferably a range of 4 parts by weight to 12 parts by weight, with respect to 1 part by weight of the alginic acid. When the blending amount of the non-reducing sugar is set to 1 part by weight or more with respect to 1 part by weight of the alginic acid, sufficient moisture retaining property is obtained and a decrease in impression accuracy can be suppressed, even when a cured product is left to stand for a longer period of time after impression taking. Further, when the blending amount of the non-reducing sugar is set to 20 parts by weight or less with respect to 1 part by weight of the alginic acid, the inhibition of the gelling reaction of the alginic acid by the non-reducing sugar during impression taking can be suppressed.

It should be noted that, in using the alginate impression material according to this embodiment, a curing material paste and a base material paste are kneaded together and used. The kneading may also be carried out manually. In general, however, the kneading is preferably carried out through the use of a dedicated kneading apparatus from the viewpoints of labor saving and automation of kneading work. Further, a mixing ratio between the curing material paste and the base material paste is not particularly limited. In general, however, the base material paste falls within preferably a range of 1 part by weight to 4 parts by weight with respect to 1 part by weight of the curing material paste. Further, those two kinds of pastes are generally stored in a sealed state by utilizing a known housing member such as a packaging bag, e.g., an aluminum pack, or a storage container in order to ensure storage stability. It should be noted that, when the alginate impression material according to this embodiment is provided to a product user such as a dentist or a dental technician, in general, there may be adopted any of such a mode that a set of a housing member containing a base material paste and a housing member containing a curing material paste is provided, and such a mode that a housing member containing a base material paste and a housing member containing a curing material paste are each individually provided. Further, other additives may also be added as necessary to the curing material paste or the base material paste. Those additives are described later.

Next, constituents of the alginate impression material according to this embodiment, and other components to be additionally used in using the alginate impression material are described.

—Alginic Acid—

Any known alginic acid, which is utilized in a conventional alginate impression material, may be utilized as the alginic acid without any particular limitation. Specific examples thereof include the above-mentioned alginic acids to be used in the alginic acid-containing aqueous composition according to this embodiment. However, of those alginic acids, an alkali metal alginate is preferably used for the base material paste, from the viewpoints of, for example, ease of availability, ease of handling, and physical properties of a cured product. Further, a mixture of two or more kinds of alginic acids may be used.

In general, the content of the alginic acid in a kneaded product falls within preferably a range of 2 wt % to 10 wt %. Thus, in the alginate impression material according to this embodiment, the amount of the alginic acid contained in the base material paste is adjusted so that the content of the alginic acid falls within the above-mentioned range in the kneaded product. Further, the molecular weight of the alginic acid is not particularly limited. In general, however, the molecular weight is preferably such a molecular weight that the viscosity of an aqueous solution containing the alginic acid at 1 wt % falls within a range of 50 cps to 100 cps, from the viewpoint that the alginic acid is used in the base material paste.

It should be noted that, in a mixed composition containing an alginic acid and water, a time-dependent decrease in viscosity is generally liable to occur. Such time-dependent decrease in viscosity shortens the estimated usable period (product lifetime) of a base material paste containing an alginic acid and water as main components. However, in the base material paste to be used in the alginate impression material according to this embodiment, that is, the alginic acid-containing aqueous composition according to this embodiment, the time-dependent decrease in viscosity is suppressed, and hence the product lifetime of the base material paste can be prolonged markedly.

It should be noted that, from the viewpoint of a marked improvement in product lifetime of the base material paste, such effect of suppressing a time-dependent decrease in viscosity can be stably obtained as long as the blending amount of the non-reducing sugar in the base material paste falls within a range of 1 part by weight to 20 parts by weight with respect to 1 part by weight of the alginic acid.

—Gelling Reaction Agent—

Any known gelling reaction agent, which is utilized in a conventional alginate impression material, may be utilized as the gelling reaction agent without any particular limitation. As the gelling reaction agent, generally a divalent or more highly valent metal compound can be used. Examples thereof include (i) calcium sulfate such as calcium sulfate dihydrate, calcium sulphate hemihydrate, or anhydrous calcium sulfate, (ii) an oxide containing a divalent or more highly valent metal such as calcium, magnesium, zinc, aluminium, iron, titanium, zirconium, or tin, and (iii) a hydroxide containing a divalent or more highly valent metal described in the item (ii). Preferred specific examples of the oxide and the hydroxide include calcium oxide, magnesium oxide, zinc oxide, titanium oxide, zirconium oxide, tin oxide, calcium hydroxide, magnesium hydroxide, zinc hydroxide, aluminium hydroxide, and iron hydroxide.

Those gelling reaction agents may be used as a mixture of two or more kinds thereof. Further, from the viewpoint that physical properties such as the curing property of a kneaded product and the elasticity of a cured product obtained by curing are made satisfactory, it is preferred to use, as the gelling reaction agent, a product obtained by blending at least one oxide selected from magnesium oxide and zinc oxide or a mixture of both the oxides in an amount within a range of 2 parts by weight to 40 parts by weight with respect to 100 parts by weight of calcium sulfate.

The blending amount of the gelling reaction agent is not particularly limited and falls within preferably a range of 10 parts by weight to 2,000 parts by weight, more preferably a range of 100 parts by weight to 1,000 parts by weight, with respect to 100 parts by weight of the alginic acid.

It should be noted that the gelling reaction agent has a function of forming a cured product through a gelling reaction between the gelling reaction agent and the alginic acid in the presence of water. In this case, the water has functions of dissolving a polyvalent metal ion such as a calcium ion from the gelling reaction agent and promoting the reaction between the gelling reaction agent and the alginic acid, and also has a function of keeping a cured product in a gel form.

—Water—

In the same manner as in the alginic acid-containing aqueous composition according to this embodiment, tap water, ion-exchange water, distilled water, or the like may be utilized as the water. When the blending amount of the water with respect to the alginic acid is too small, a gelling reaction between an alginic acid and a gelling reaction agent such as a polyvalent metal ion may occur inhomogeneously, or the gelling reaction may proceed slowly. On the other hand, when the blending amount of the water with respect to the alginic acid is too large, a gelling reaction may hardly occur, or the strength of a gel-like cured product after gelling may lower. As for the blending amount of the water with respect to the alginic acid, the amount of the water to be used in producing a kneaded product falls within preferably a range of 1 part by weight to 40 parts by weight, preferably a range of 1 part by weight to 30 parts by weight, still more preferably a range of 5 parts by weight to 20 parts by weight, with respect to 1 part by weight of the alginic acid in the kneaded product.

—Non-Reducing Sugar—

As the non-reducing sugar, the same one as that used in the alginic acid-containing aqueous composition according to this embodiment may be appropriately used. However, when the molecular weight of the non-reducing sugar is too large, the alginic acid and the non-reducing sugar may form a hydrogen bond to cause aggregation. Thus, from this viewpoint, as the non-reducing sugar, a sugar formed of 2 to 10 monosaccharide molecules bonded via a glycosidic bond is preferably used, and a disaccharide is more preferably used. In addition, from the viewpoints of impression accuracy and moisture retaining property, trehalose is particularly preferred among the disaccharides.

—Poorly Water-Soluble Organic Solvent—

The poorly water-soluble organic solvent is used for the pasting of a curing material paste containing a gelling reaction agent. That is, the poorly water-soluble organic solvent has a function of forming a paste when being mixed with a gelling reaction agent. In general, the gelling reaction agent has property of being cured through a reaction with water. Hence, in order to store the gelling reaction agent in a pasty form stably over a long period of time, a poorly water-soluble solvent which is hardly hydrated, i.e., a poorly water-soluble organic solvent is used as the solvent to be used for the pasting. Herein, the "poorly water-soluble organic solvent" means a liquid having a solubility of 5 g or less in 100 g of water at a temperature of 20° C. It should be noted that the solubility of the poorly water-soluble organic solvent is preferably 3 g or less. Any known liquid may be utilized as the poorly water-soluble organic solvent as long as the liquid shows the solubility. Examples of such liquid include a hydrocarbon compound, an aliphatic alcohol, a cyclic alcohol, a fatty acid, a fatty acid salt, a fatty acid ester, and a hydrophobic polymer. Suitable examples of the various poorly water-soluble organic solvents are shown below.

First, as the hydrocarbon compound, both a chain compound and a cyclic compound can be used. Examples of the hydrocarbon compound include: aliphatic linear hydrocarbon compounds such as hexane, heptane, octane, nonane, decane, undecane, dodecane, tridecane, tetradecane, pentadecane, kerosine, 2,7-dimethyloctane, and 1-octene; alicyclic hydrocarbon compounds such as cycloheptane and cyclononane; and liquid paraffin which is a mixture of liquid saturated hydrocarbons.

Examples of the aliphatic alcohol include saturated aliphatic alcohols such as 1-hexanol and 1-octanol, and unsaturated aliphatic alcohols such as citronellol and oleyl alcohol. Examples of the cyclic alcohol include benzyl alcohol and metacresol.

Examples of the fatty acid include saturated fatty acids such as hexanoic acid and octanoic acid, and unsaturated fatty acids such as oleic acid and linoleic acid. Besides, examples of the fatty acid ester include vegetable oils such as ethyl octanoate, butyl phthalate, oleic acid glyceride, olive oil, and sesame oil, and animal fats such as liver oil and whale oil. An example of the hydrophobic polymer is a polysiloxane (so-called silicone oil). Specific examples thereof include a polydimethylsiloxane, a polymethylphenylsiloxane, a polymethyl hydrogen siloxane, and a polyphenyl hydrogen siloxane.

In addition, when a manufacturing cost, living body damaging property, an influence on gustatory sensation in taking an impression of teeth, and the like are taken into consideration, it is more preferred to use a hydrocarbon compound or a hydrophobic polymer and it is particularly preferred to use liquid paraffin or silicone oil, out of the poorly water-soluble organic solvents listed in the foregoing. Further, the poorly water-soluble organic solvents may be used as a mixture of two or more kinds thereof.

The blending amount of the poorly water-soluble organic solvent is not particularly limited. In general, however, the blending amount falls within preferably a range of 10 parts by weight to 200 parts by weight, more preferably a range of 20 parts by weight to 100 parts by weight, with respect to 100 parts by weight of the gelling reaction agent.

—Additive—

The alginate impression material according to this embodiment may be blended with various additives as necessary in addition to the above-mentioned components. Examples of the additive include a gelling regulator, a filler, a surfactant, an inorganic fluorine compound, an amino acid compound, an unsaturated carboxylic acid polymer, a flavor, a colorant, an antimicrobial agent, a preservative, and a pH adjustor.

It should be noted that those additives may be appropriately added to any one or both of the base material paste and the curing material paste. However, the filler is preferably added to both of the base material paste and the curing material paste, and the gelling regulator and the surfactant are each preferably added to the curing material paste.

In the case of using the gelling regulator, the speed of a reaction between the alginic acid and the gelling reaction agent may be regulated (delayed). This makes it easy to adjust a curing time substantially in correspondence with an operation time required from the mixing/kneading of constituents of the alginate impression material to impression taking in the oral cavity.

As the gelling regulator, known gelling regulators can be used without any limitation. Typical examples of the gelling regulator include (i) alkali metal-containing phosphoric acid salts such as trisodium phosphate, tripotassium phosphate, sodium pyrophosphate, and sodium tripolyphosphate, (ii) alkali metal-containing oxalic acid salts such as sodium oxalate and potassium oxalate, and (iii) alkali metal-containing carbonic acid salts such as sodium carbonate and potassium carbonate. Two or more kinds of those gelling regulators may be used as a mixture.

The blending amount of the gelling regulator may be appropriately selected depending on, for example, other blend components and a required curing time, and falls within preferably a range of 1 part by weight to 30 parts by weight, more preferably a range of 3 parts by weight to 15 parts by weight, with respect to 100 parts by weight of the alginic acid. The control of the blending amount of the gelling regulator within the above-mentioned range makes it easy to adjust a curing time substantially in correspondence with an operation time, and allows a cured product to be cured sufficiently.

Further, a filler is preferably used in order to adjust the physical properties of a cured product. As the filler, a clay mineral such as diatomaceous earth or talc is preferably used, and a metal or semimetal oxide such as silica or alumina may also be used. The blending amount of the filler is not particularly limited and falls within preferably a range of 50 parts by weight to 2,000 parts by weight, more preferably a range of 100 parts by weight to 1,000 parts by weight, with respect to 100 parts by weight of the alginic acid.

Further, for various purposes, for example, for the purposes of dust suppression, an improvement in mixing property in water, pasting of a gelling reaction agent component containing calcium sulfate or the like as a main component, and the like, a surfactant may also be used. Any known surfactant may be utilized as the surfactant without no particular limitation, and any of an anionic surfactant, a cationic surfactant, an amphoteric surfactant, and a nonionic surfactant may be used.

Examples of the anionic surfactant include an alkylsulfonic acid salt, an alkylbenzenesulfonic acid salt, and an alkyl ether carboxylic acid salt. Examples of the cationic surfactant include an alkylamine salt and a quaternary ammonium salt. An example of the amphoteric surfactant is aminocarboxylic acid salt. Examples of the nonionic surfactant include a polyoxyethylene alkyl ether, a polyoxyethylene alkyl phenyl ether, a polyoxyethylene-polyoxypropylene block polymer, a polyoxyethylene glycerin fatty acid ester, a polyoxyglycerin fatty acid ester, a sorbitan fatty acid ester, a sucrose ester, a polyoxydiethylene alkylamine, and a block polymer of a polysiloxane and a polyoxyethylene.

The blending amount of the surfactant is not particularly limited and falls within preferably a range of 0.1 part by weight to 300 parts by weight, more preferably a range of 1 part by weight to 100 parts by weight, with respect to 100 parts by weight of the alginic acid.

Further, from the viewpoint of preventing the surface roughening of a gypsum model during impression taking or during gypsum model manufacture, it is preferred to blend an inorganic fluorine compound such as potassium titanium fluoride or potassium silicofluoride or an amino acid compound such as an amino acid/formaldehyde condensate. Further, it is preferred to blend an unsaturated carboxylic acid polymer in order to easily control the speed of a time-dependent change in viscosity of the kneaded product in the mixing/kneading of constituents of the alginate impression material. Further, anyone kind or a plurality of kinds of additives selected from a flavor, a colorant, a pH adjustor, an antimicrobial agent, a preservative, and the like may be blended as necessary.

—Manufacturing Method—

A manufacturing method for the alginate impression material according to this embodiment is not particularly limited, and a known manufacturing method may be appropriately selected. Specifically, a base material paste and a curing material paste may be manufactured through the use of a known agitation mixer, which may be utilized in paste manufacture. In this case, examples of the agitation mixer which may be utilized include a rotating container type mixing kneader such as a ball mill, and a fixed container type mixing kneader having a horizontal axis or a vertical axis such as a ribbon mixer, a Ko-kneader, an internal mixer, a a screw kneader, a Henschel mixer, a versatile mixer, a Loedige mixer, or a butterfly mixer. Further, in the manufacture of a base material paste, when a first step of dissolving a component having relatively high solubility in water, such as a non-reducing sugar, is carried out, and then a downstream step of dissolving a component having relatively low solubility in water, such as an alginic acid, sequentially or collectively is carried out, there may be utilized such an agitation apparatus that no strong shearing force is applied to the component to be dissolved or a solution having the component dissolved therein in carrying out the first step. As such agitation apparatus, there may be used, for example, a transferable agitator, a vertical agitator, and a side entering agitator, equipped with various impellers, and a line agitator. In addition, in the manufacture of a base material paste and a curing material paste, the various mixing kneaders may be utilized in combination of two or more kinds thereof.

—Use Aspect of Alginate Impression Material—

In using the alginate impression material according to this embodiment, in general, at least, a kneaded product is produced from the alginate impression material according to this embodiment, and then the kneaded product is mounted on a dedicated tray. Then, the kneaded product mounted on the tray is pressed against a target such as teeth to take an impression. After that, the kneaded product after impression taking is cured to form a cured product, and then a downstream step such as a step of producing a gypsum model based on the cured product is further carried out. In this case, a known tray may be utilized as the tray without any limitation. In general, however, a tray made of a metal or a tray made of a resin is utilized. A material for the tray made of a metal is exemplified by stainless, a tin alloy, aluminum, and brass subjected to a plating treatment or resin coating. It should be noted that, in the case of using the alginate impression material according to this embodiment, the kneaded product is well retained in any of the trays made of a metal. Further, a material for the tray made of a resin is exemplified by polymethacrylic acid ester.

EXAMPLES

Hereinafter, the present invention is described by way of examples and comparative examples in order to specifically describe the present invention. However, the present invention is by no means limited by these examples and comparative examples.

a thermostat bath at 50° C. for 7 days. The composition was measured for its viscosity again after storage for 7 days. From the measured values for the viscosities of the composition before and after a heat treatment, a viscosity remaining rate (%) was calculated according to the following equation (2). Table 1 shows the results of the composition and viscosity remaining rate of the composition.

$$\text{Viscosity remaining rate (\%)}=(\text{Viscosity after storage at 50° C. for 7 days})\div(\text{Viscosity immediately after manufacture})\times 100 \quad \text{Equation (2)}$$

Examples A2 to A4 and Comparative Examples A1 to A3

Alginic acid-containing aqueous compositions having different compositions shown in Table 1 were prepared in conformity with the method of Example A1. Table 1 shows the results of the composition and viscosity remaining rate of each of the compositions. All of sodium alginate and potassium alginate used are manufactured by KIMICA Corporation, any of which has an M/G ratio of 1.2.

TABLE 1

|  |  | Example A1 | Example A2 | Example A3 | Example A4 | Comparative Example A1 | Comparative Example A2 | Comparative Example A3 |
|---|---|---|---|---|---|---|---|---|
| Alginic acid or derivative thereof (A) | Alginic acid | 1 | — | — | — | 1 | — | — |
|  | Sodium alginate | — | 1 | — | — | — | 1 | — |
|  | Potassium alginate | — | — | 1 | 1 | — | — | 1 |
| Water (B) | Distilled water | 1,000 | 1,000 | 1,000 | 1,000 | 1,000 | 1,000 | 1,000 |
| Non-reducing sugar (C) | Trehalose (disaccharide) | 10 | 10 | 10 | — | — | — | — |
|  | Sucrose (disaccharide) | — | — | — | 10 | — | — | — |
| Viscosity (mPa·s) | Immediately after manufacture | 3.20 | 3.26 | 8.93 | 8.94 | 3.20 | 3.26 | 8.95 |
|  | After storage at 50° C. for 7 days | 2.95 | 3.07 | 7.77 | 7.73 | 2.76 | 2.78 | 7.13 |
| Viscosity remaining rate (%) |  | 92.2 | 94.2 | 87.0 | 86.5 | 86.3 | 85.3 | 79.7 |

I. Evaluations on Viscosity Remaining Rate and Curing Property

An aqueous composition containing at least an alginic acid was evaluated for its viscosity remaining rate and curing property by each of Examples A1 to A26 and Comparative Examples A1 to A13 below.

Example A1

1.0 g of alginic acid (manufactured by KIMICA Corporation, M/G ratio=1.2) was dissolved with stirring in 1,000 g of distilled water. After the dissolution of alginic acid, 10 g of trehalose as a non-reducing sugar were added and dissolved.

The composition prepared by the above-mentioned method was measured for its viscosity in a thermostat water bath at 23° C. through the use of a Cannon-Fenske viscometer (manufactured by SIBATA SCIENTIFIC TECHNOLOGY LTD.) as one kind of capillary viscometer, and the viscosity was defined as a viscosity immediately after manufacture. After that, a transparent glass bottle was filled with a 50-mL aliquot of the composition, sealed hermetically, and stored in The compositions of Comparative Examples A1 to A3 are free of any non-reducing sugar. A time-dependent decrease in viscosity was observed in any of the compositions. On the other hand, the compositions of Examples A1 to A4 each contain alginic acid or a derivative thereof, water, and a non-reducing sugar. A time-dependent decrease in viscosity was found to be suppressed in any of the compositions as compared to the compositions of Comparative Examples A1 to A3 free of any non-reducing sugar.

Examples A5 to A9

Alginic acid-containing aqueous compositions having different compositions shown in Table 2 were prepared in conformity with the method of Example A1. Table 2 shows the results of the composition and viscosity remaining rate of each of the compositions.

TABLE 2

|  |  | Example A5 | Example A6 | Example A7 | Example A8 | Example A9 |
|---|---|---|---|---|---|---|
| Alginic acid or derivative thereof (A) | Potassium alginate | 1 | 1 | 1 | 1 | 1 |
| Water (B) | Distilled water | 1,000 | 1,000 | 1,000 | 1,000 | 1,000 |
| Non-reducing sugar (C) | α-Cyclodextrin (hexasaccharide) | 10 | — | — | — | — |
|  | β-Cyclodextrin (heptasaccharide) | — | 10 | — | — | — |
|  | γ-Cyclodextrin (octasaccharide) | — | — | 10 | — | — |
|  | ε-Cyclodextrin (decasaccharide) | — | — | — | 10 | — |
|  | ζ-Cyclodextrin (undecasaccharide) | — | — | — | — | 10 |
| Viscosity (mPa·s) | Immediately after manufacture | 8.94 | 8.94 | 8.94 | 8.95 | 8.95 |
|  | After storage at 50° C. for 7 days | 7.71 | 7.68 | 7.66 | 7.62 | 7.50 |
| Viscosity remaining rate (%) |  | 86.2 | 85.9 | 85.7 | 85.1 | 83.8 |

The compositions of Examples A5 to A9 each contain alginic acid or a derivative thereof, water, and a non-reducing sugar. A time-dependent decrease in viscosity was found to be suppressed in any of the compositions as compared to the composition of Comparative Example A3 free of any non-reducing sugar.

Comparative Examples A4 to A9

Alginic acid-containing aqueous compositions having different compositions were each prepared by blending a reducing sugar in place of the non-reducing sugar of Example A1. Table 3 shows the results of the composition and viscosity remaining rate of each of the compositions.

TABLE 3

|  |  | Comparative Example A4 | Comparative Example A5 | Comparative Example A6 | Comparative Example A7 | Comparative Example A8 | Comparative Example A9 |
|---|---|---|---|---|---|---|---|
| Alginic acid or derivative thereof (A) | Alginic acid | 1 | — | — | — | — | — |
|  | Sodium alginate | — | 1 | — | — | — | — |
|  | Potassium alginate | — | — | 1 | 1 | 1 | 1 |
| Water (B) | Distilled water | 1,000 | 1,000 | 1,000 | 1,000 | 1,000 | 1,000 |
| Reducing sugar | Glucose | 10 | 10 | 10 | — | — | — |
|  | Galactose | — | — | — | 10 | — | — |
|  | Maltose | — | — | — | — | 10 | — |
|  | Lactose | — | — | — | — | — | 10 |
| Viscosity (mPa·s) | Immediately after manufacture | 3.20 | 3.26 | 8.94 | 8.93 | 8.93 | 8.93 |
|  | After storage at 50° C. for 7 days | 2.01 | 2.04 | 5.71 | 6.15 | 6.79 | 6.08 |
| Viscosity remaining rate (%) |  | 62.8 | 62.6 | 63.9 | 68.9 | 76.0 | 68.1 |

The compositions of Comparative Examples A4 to A9 each contain a reducing sugar blended in place of the non-reducing sugar. A time-dependent decrease in viscosity was found to be promoted in any of the compositions as compared to the compositions of Comparative Examples A1 to A3 free of any reducing sugar.

Examples A10 to A13

Alginic acid-containing aqueous compositions having different compositions shown in Table 4 were prepared in conformity with the method of Example A1. Table 4 shows the results of the composition and viscosity remaining rate of each of the compositions.

TABLE 4

|  |  | Example A10 | Example A11 | Example A12 | Example A13 |
|---|---|---|---|---|---|
| Alginic acid or derivative thereof (A) | Potassium alginate | 1 | 1 | 1 | 1 |
| Water (B) | Distilled water | 1,000 | 1,000 | 1,000 | 1,000 |
| Non-reducing sugar (C) | Trehalose (disaccharide) | 10 | 10 | 10 | 10 |

TABLE 4-continued

|  |  | Example A10 | Example A11 | Example A12 | Example A13 |
|---|---|---|---|---|---|
| Reducing sugar | Glucose | 1 | — | 0.05 | — |
|  | Lactose | — | 1 | — | 0.05 |
| Viscosity (mPa·s) | Immediately after manufacture | 8.93 | 8.93 | 8.93 | 8.93 |
|  | After storage at 50° C. for 7 days | 7.45 | 7.48 | 7.65 | 7.68 |
| Viscosity remaining rate (%) |  | 83.4 | 83.8 | 85.7 | 86.0 |

The compositions of Examples A10 to A13 each contain a reducing sugar blended in addition to the non-reducing sugar. A time-dependent decrease in viscosity was found to be suppressed in any of the compositions as compared to the composition of Comparative Example A3 free of any non-reducing sugar.

Examples A14 to A19

Alginic acid-containing aqueous compositions having different compositions shown in Table 5 were prepared in conformity with the method of Example A1. Table 5 shows the results of the composition and viscosity remaining rate of each of the compositions.

TABLE 5

|  |  | Example A14 | Example A15 | Example A16 | Example A17 | Example A18 | Example A19 |
|---|---|---|---|---|---|---|---|
| Alginic acid or derivative thereof (A) | Potassium alginate | 1 | 1 | 1 | — | — | — |
|  | Sodium alginate | — | — | — | 1 | 1 | 1 |
| Water (B) | Distilled water | 1,000 | 1,000 | 1,000 | 1,000 | 1,000 | 1,000 |
| Non-reducing sugar (C) | Trehalose (disaccharide) | 0.05 | 1 | 100 | 0.05 | 1 | 100 |
| Viscosity (mPa·s) | Immediately after manufacture | 8.94 | 8.94 | 8.93 | 3.26 | 3.26 | 3.26 |
|  | After storage at 50° C. for 7 days | 7.24 | 7.37 | 7.80 | 2.84 | 2.90 | 3.09 |
| Viscosity remaining rate (%) |  | 81.0 | 82.4 | 87.3 | 87.1 | 89.0 | 94.8 |

The compositions of Examples A14 to A19 each contain alginic acid or a derivative thereof, water, and a non-reducing sugar. A time-dependent decrease in viscosity was found to be suppressed in any of the compositions as compared to the compositions of Comparative Examples A2 and A3 free of any non-reducing sugar.

Example A20

1.0 g of sodium alginate (manufactured by KIMICA Corporation) was dissolved with stirring in 20 g of distilled water. After the dissolution of sodium alginate, 1.0 g of trehalose as a non-reducing sugar was added and dissolved. After that, 3.0 g of celite were further added and the mixture was formed into a paste. Thus, a base material paste for a dental alginate impression material was prepared.

The base material paste prepared by the above-mentioned method was measured for its viscosity at 23° C. through the use of a spiral viscometer (manufactured by Malcom Co., Ltd.), and the viscosity was defined as a viscosity immediately after manufacture. The prepared base material paste was mixed with a curing material paste at a weight ratio of 3:1 and the curing property was evaluated. Evaluation criteria for the curing property are as follows: a case where the composition was cured is represented by Symbol "A"; and a case where the composition was not completely cured is represented by Symbol "B". A curing material paste "Tokuyama AP-1" manufactured by Tokuyama Dental Corporation was used as the curing material paste. After that, a transparent glass bottle was filled with a 100-mL aliquot of the composition, sealed hermetically, and stored in a thermostat bath at 50° C. for 7 days. The composition was measured for its viscosity again after storage for 7 days. From the measured values for the viscosities of the composition before and after a heat treatment, a viscosity remaining rate (%) was calculated according to the mathematical equation 1. Table 6 shows the results of the composition and viscosity remaining rate of the composition.

Example A21 and Comparative Examples A10 to A13

Alginic acid-containing aqueous compositions having different compositions shown in Table 6 were prepared in conformity with the method of Example A20. Table 6 shows the results of the composition, viscosity remaining rate, and curing property of each of the compositions.

TABLE 6

|  |  | Example A20 | Example A21 | Comparative Example A10 | Comparative Example A11 | Comparative Example A12 | Comparative Example A13 |
|---|---|---|---|---|---|---|---|
| Alginic acid or derivative thereof (A) | Sodium alginate | 1 | — | 1 | — | 1 | 1 |
|  | Potassium alginate | — | 1 | — | 1 | — | — |
| Water (B) | Distilled water | 20 | 20 | 20 | 20 | 20 | 20 |
| Non-reducing sugar (C) | Trehalose (disaccharide) | 1 | 1 | — | — | — | — |
| Filler (D) | Celite | 3 | 3 | 3 | 3 | 3 | 3 |
| Reducing sugar | Glucose | — | — | — | — | 1 | — |
|  | Lactose | — | — | — | — | — | 1 |
| Viscosity (Pa · s) | Immediately after manufacture | 78.9 | 79.1 | 78.9 | 79.1 | 78.9 | 78.9 |
|  | After storage at 50° C. for 7 days | 63.7 | 60.0 | 56.8 | 52.2 | 34.0 | 36.2 |
| Viscosity remaining rate (%) |  | 80.7 | 75.9 | 72.0 | 66.0 | 43.1 | 45.9 |
| Curing property |  | A | A | A | A | A | A |

The compositions of Comparative Examples A10 to A13 are free of any non-reducing sugar. A time-dependent decrease in viscosity was observed in any of the compositions. On the other hand, the compositions of Examples A20 and A21 each contain alginic acid or a derivative thereof, water, and a non-reducing sugar. A time-dependent decrease in viscosity was found to be suppressed in any of the compositions as compared to the compositions of Comparative Examples A10 and A11 free of any non-reducing sugar.

Examples A22 to A26

Alginic acid-containing aqueous compositions having different compositions shown in Table 7 were prepared in conformity with the method of Example A20. Table 7 shows the results of the composition, viscosity remaining rate, and curing property of each of the compositions.

TABLE 7

|  |  | Example A22 | Example A23 | Example A24 | Example A25 | Example A26 |
|---|---|---|---|---|---|---|
| Alginic acid or derivative thereof (A) | Sodium alginate | 1 | 1 | — | — | — |
|  | Potassium alginate | — | — | 1 | 1 | 1 |
| Water (B) | Distilled water | 20 | 20 | 20 | 20 | 20 |
| Non-reducing sugar (C) | Trehalose (disaccharide) | 5 | 10 | 5 | 10 | 100 |
| Filler (D) | Celite | 3 | 3 | 3 | 3 | 3 |
| Viscosity (Pa · s) | Immediately after manufacture | 78.7 | 68.9 | 78.9 | 69.1 | 65.3 |
|  | After storage at 50° C. for 7 days | 64.9 | 60.0 | 64.7 | 59.8 | 59.1 |
| Viscosity remaining rate (%) |  | 82.5 | 87.1 | 82.0 | 86.5 | 90.5 |
| Curing property |  | A | A | A | A | B |

The compositions of Examples A22 to A26 each contain alginic acid or a derivative thereof, water, and a non-reducing sugar. A time-dependent decrease in viscosity was found to be suppressed in any of the compositions as compared to the compositions of Comparative Examples A10 and A11 free of any non-reducing sugar. However, the composition of Example A26, in which the addition amount of trehalose as the non-reducing sugar was too large, was not cured even when mixed with the curing material paste.

II. Evaluations on Surface Lubrication Property, Compatible Deformation, and Viscosity Remaining Rate A cured product obtained by mixing a base material paste with a curing material paste was evaluated for its surface lubrication property and compatible deformation by examples and comparative examples shown below. Further, an aqueous composition containing at least an alginic acid used as the base material paste was evaluated for its viscosity remaining rate.

<<Abbreviated Names of Raw Materials>>

Abbreviated names of various raw materials used for the production of alginate impression materials of examples and comparative examples to be described later are as described below.

1. Alginic Acid
ARK: potassium alginate
ARNa: sodium alginate
2. Gelling Reaction Agent
ZnO: zinc oxide
MgO: magnesium oxide
3. Non-Reducing Sugar
Cdexα: α-cyclodextrin
Cdexβ: β-cyclodextrin
4. Poorly-Water-Soluble Organic Solvent
Hex: n-hexane
5. Surfactant
Dec-Gly: decaglyceryl trioleate
6. Gelling Regulator
P3Na: trisodium phosphate
7. Filler
MT-10: amorphous silica having a particle diameter of 0.02 μm (methyltrichlorosilane treated product)
8. Others
FTK: titanium potassium fluoride <<Evaluation Methods and Evaluation Criteria>>

An evaluation method and evaluation criteria for "surface lubrication property" and evaluation methods for "compatible deformation" and "base material paste viscosity remaining rate" for samples of examples and comparative examples to be described later are as described below.

(1) Surface Lubrication Property

The surface lubrication property was evaluated according to the following procedures. First, the preliminarily prepared base material paste and curing material paste were kneaded together through the use of an automatic alginate impression material mixer AP Mixer II (manufactured by Tokuyama Dental Corporation).

Next, the kneaded product was poured into a columnar mold (outer diameter: 60 mm, inner diameter: 52 mm, height: 10 mm), the kneaded product protruding from an opening portion of the columnar mold was removed with a spatula, and the surface was uniformized so as to be coincident with the opening plane of the opening portion. The kneaded product was left to stand in this state for 3 minutes. After that, the surface of the cured product obtained by curing the kneaded product was visually observed to evaluate the surface lubrication property. Further, the cured product was transferred to a moist box (hermetically sealed container containing water at the bottom) maintained at a humidity of 80% or more. The cured product was left to stand for a predetermined period of time and then evaluated for its surface lubrication property. It should be noted that the surface lubrication property shown in the table to be described later was evaluated according to the following evaluation criteria. Further, "Immediately after" shown in the "Surface lubrication property" column in the table to be described later shows the visual observation results of the cured product immediately after curing (cured product stored in the moist box for 0 minutes), "After 1 hour" shows the visual observation results of the cured product after the cured product has been left to stand in the moist box for 1 hour, and "After 3 days" shows the visual observation results of the cured product after the cured product has been left to stand in the moist box for 3 days.

—Evaluation Criteria for Surface Lubrication Property—
A: A surface of a cured product is glossy as if wet and is very smooth.
B: A surface of a cured product is not glossy but is very smooth.
C: A surface of a cured product is not glossy and is rough.
D: A surface of a cured product is dried up by drying and has cracks in places.

(2) Compatible Deformation

A pair of molds illustrated in FIG. 1 were used in the evaluation of the compatible deformation. In this case, as illustrated in FIG. 1, the pair of molds used in the evaluation of the compatible deformation include a first mold 10 and a second mold 20. The first mold 10 has two recessed portions 12R, 12L, and the second mold 20 has two protruded portions 22R, 22L. Further, the first mold 10 and the second mold 20 each have such dimensional accuracy that, when the first mold 10 and the second mold 20 are fitted together so that the recessed portion 12R matches the protruded portion 22R and the recessed portion 12L matches the protruded portion 22L as illustrated in FIG. 1, both the molds can be fitted together with substantially no space therebetween. It should be noted that the shape and dimension of the protruded portions 22R, 22L are determined on the assumption of the production of a bridge crown, and each of the protruded portions 22R, 22L has a height H of 10 mm and a top surface width W of 8 mm.

Next, the preliminarily prepared base material paste and curing material paste were kneaded together through the use of an automatic alginate impression material mixer AP Mixer II (manufactured by Tokuyama Dental Corporation).

After that, the kneaded product was poured into a tray made of a resin having such a size that the second mold 20 was able to be housed completely, and the surface was then uniformized. Then, at the time when the uniformization of the surface of the kneaded product was finished, a button of a stopwatch was pushed to start time measurement. Subsequently, after the lapse of 20 seconds, the second mold 20 was brought into contact with the kneaded product placed in the tray made of a resin under pressure, with the surface having the protruded portions 22R, 22L provided thereon down. The kneaded product was cured by being left to stand in this state for 3 minutes. After that, the second mold 20 was removed to take an impression.

Next, the cured product after the impression taking was left to stand in a moist box formed of a hermetically sealed container containing water at the bottom and kept at a humidity of 80% or more for a predetermined period of time. Then, high strength gypsum for impression model production (NEW FUJIROCK manufactured by GC) was poured into an impression taking portion of the cured product taken out from the moist box and then left to stand for 1 hour to cure the gypsum. Alternatively, high strength gypsum was poured directly into the cured product after the impression taking and then left to stand for 1 hour to cure the gypsum. Thus, a plurality of kinds of gypsum models of the second mold 20 left to stand in the moist box for different periods of time were obtained.

Figure 2:
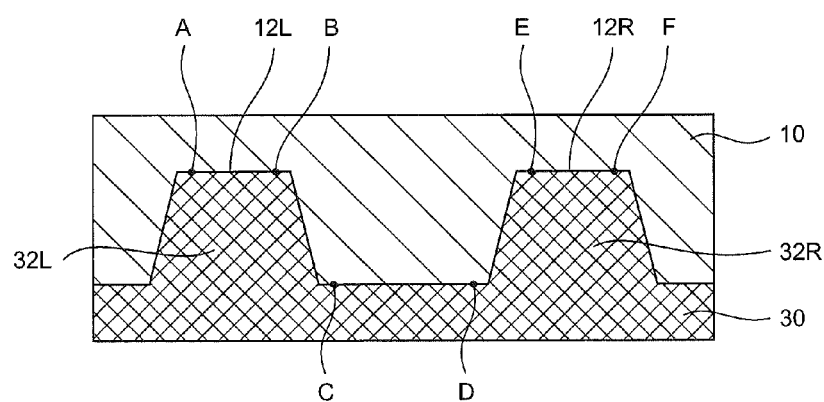
FIG. 2 A schematic view illustrating an evaluation method for compatible deformation.

After that, as illustrated in FIG. 2, in a state in which the surface of a gypsum model 30 on the side where protruded portions 32R, 32L were provided was fitted to the surface of the first mold 10 on the side where the recessed portions 12R, 12L were provided, a gap length to be formed between the gypsum model 30 and the first mold 10 was measured through the use of a microscope (laser microscope VK-8700 manufactured by KEYENCE CORPORATION). It should be noted that, as illustrated in FIG. 2, the gap length was measured at each of the following points: (1) two points in the vicinity of both the ends between the bottom surface of the recessed portion 12L and the top surface of the protruded portion 32L opposed to the bottom surface (positions represented by symbols A and B in FIG. 2); (2) two points in the vicinity of both the ends between the surface of the first mold 10 and the surface of the gypsum model 30 opposed to the surface in a region between the protruded portion 32R and the protruded portion 32L (positions represented by symbols C and D in FIG. 2); and (3) two points in the vicinity of both the ends between the bottom surface of the recessed portion 12R and the top surface of the protruded portion 32R opposed to the bottom surface (positions represented by symbols E and F in FIG. 2). Then, an average value of the six gap lengths measured at Point A to Point F was determined as "compatible deformation." It should be noted that, in FIG. 2, when the second mold 20 is used in place of the gypsum model 30, the "compatible deformation" determined in the same manner as in the case described above is 5.0 μm.

Further, "Immediately after" shown in the "Compatible deformation" column in the table to be described later shows the results in the case where the gypsum model 30 was produced through the use of the cured product immediately after curing (cured product stored in the moist box for 0 minutes). Further, "After 30 minutes," "After 1 hour," "After 5 hours," "After 1 day," and "After 3 days" shown in the "Compatible deformation" column in the table to be described later show the results in the case where the gypsum model 30 was produced through the use of the resultant cured product after the cured product had been stored in the moist box for 30 minutes, 1 hour, 5 hours, 1 day, and 3 days, respectively.

(3) Base Material Paste Viscosity Remaining Rate

The prepared base material paste (about 240 ml) was loaded into a beaker made of glass (volume: 300 ml). Then, the beaker was left to stand in an incubator set to a temperature of 25° C. for about 1 hour. After that, the base material paste was measured for its viscosity (initial viscosity Vi, Poise) in an incubator through the use of a rotational viscometer (Viscotester VT-04F manufactured by RION). Next, the base material paste sample measured for its initial viscosity Vi was stored in an incubator set to a temperature of 50° C. After the lapse of a predetermined period of time, the sample was taken out and left to stand in an incubator at 25° C. for 1 hour. Then, the base material paste was measured for its viscosity (V50, Poise) by the same method. It should be noted that a base material paste viscosity remaining rate after the lapse of a predetermined period of time (1 week or 3 weeks) was determined based on the following equation (3). Thus, when the base material paste is not stored an incubator set to a temperature of 50° C., the base material paste viscosity remaining rate is 100% because the viscosity V50 is a value substantially approximate to the initial viscosity Vi.

Base material paste viscosity remaining rate
(%)=100×[V50/Vi]   Equation (3)

It should be noted that "Initial," "After 1 week," and "After 3 weeks" shown in the "Base material paste viscosity remaining rate" column shown in the table to be described later mean that the base material paste sample was stored in an incubator set to 50° C. for 0 minutes (i.e., a case where the storage in the incubator set to 50° C. is not carried out), 1 week, and 3 weeks, respectively.

<<Evaluations on Surface Lubrication Property and Compatible Deformation>>

Example B1

10 g of ARK as an alginic acid, 150 g of distilled water as water, and 60 g of sucrose as a non-reducing sugar were weighed and kneaded together through the use of a small kneader (I-ko mixer manufactured by I-ko Industrial Co., Ltd.) for 1 hour to prepare a base material paste. Next, 40 g of anhydrous gypsum as a gelling reaction agent and 20 g of liquid paraffin as a poorly water-soluble organic solvent were weighed and kneaded together through the use of a small kneader for 1 hour to prepare a curing material paste. The whole of the resultant pastes was kneaded together through the use of an automatic alginate impression material mixer AP Mixer II. After that, the resultant kneaded product was used and evaluated for its surface lubrication property and compatible deformation.

Examples B2 to B4

Kneaded products were each obtained by preparing a base material paste and a curing material paste and kneading the pastes together in the same manner as in Example B1 except that the composition of the alginate impression material was changed to one shown in Table 8. After that, each of the resultant kneaded products was used and evaluated for its surface lubrication property and compatible deformation.

Example B5

10 g of ARK as an alginic acid, 150 g of distilled water as water, 60 g of sucrose as a non-reducing sugar, and 5.8 g of diatomaceous earth as another component were weighed and kneaded together through the use of a small kneader for 1 hour to prepare a base material paste. Next, 40 g of anhydrous gypsum as a gelling reaction agent and 20 g of liquid paraffin as a poorly water-soluble organic solvent, and 1.0 g of P3Na, 3.2 g of Dec-Gly, 4.4 g of FTK, 29.2 g of diatomaceous earth, and 3.0 g of MT-10 as other components were weighed and kneaded together through the use of a small kneader for 1 hour to prepare a curing material paste. The whole of the resultant pastes was kneaded together through the use of an automatic alginate impression material mixer AP Mixer II. After that, the resultant kneaded product was used and evaluated for its surface lubrication property and compatible deformation.

Example B6 to Example B26

Kneaded products were each obtained by preparing a base material paste and a curing material paste and kneading the pastes together in the same manner as in Example B5 except that the composition of the alginate impression material was changed to one shown in Table 8 to Table 10. After that, each of the resultant kneaded products was used and evaluated for its surface lubrication property and compatible deformation.

Examples B27 to B29 and Comparative Examples B1 to B4

Kneaded products were each obtained by preparing a base material paste and a curing material paste and kneading the pastes together in the same manner as in Example B1 except that the composition of the alginate impression material was changed to one shown in Table 11. After that, each of the resultant kneaded products was used and evaluated for its surface lubrication property and compatible deformation.

(Evaluation Results)

Table 8 to Table 11 show the compositions of the alginate impression materials of Example B1 to Example B29 and Comparative Example B1 to Comparative Example B4. Further, Table 12 shows the evaluation results of the surface lubrication property and compatible deformation of each of the samples of Example B1 to Example B26, and Table 13 shows the evaluation results of the surface lubrication property and compatible deformation of each of the samples of Examples B27 to B29 and Comparative Examples B1 to B4.

TABLE 8

| | Alginate impression material composition/parts by mass | | | | | | | | | | | | | | Base material/curing |
|---|---|---|---|---|---|---|---|---|---|---|---|---|---|---|---|
| | Curing material | | | | | | | | Base material | | | | | | |
| | Gelling reaction agent | | | | | Poorly water-soluble organic solvent | | Alginic acid salt | | Water | Non-reducing sugar | | | | |
| | Anhydrous gypsum | Dihydrated gypsum | ZnO | MgO | HeX | Liquid paraffin | Others | ARK | ARNa | Distilled water | Sucrose | Trehalose | Cdex α | Cdex β | Others | material mixing ratio |
| Example B1 | 400 | — | — | — | — | 200 | — | 100 | — | 1,500 | 600 | — | — | — | — | 3.7 |
| Example B2 | 400 | — | — | — | — | 200 | — | 100 | — | 1,500 | — | 600 | — | — | — | 3.7 |
| Example B3 | 400 | — | — | — | — | 200 | — | 100 | — | 1,500 | — | — | 600 | — | — | 3.7 |
| Example B4 | 400 | — | — | — | — | 200 | — | 100 | — | 1,500 | — | — | — | 600 | — | 3.7 |
| Example B5 | 400 | — | — | — | — | 200 | Dec-Gly (32), P3Na (10), FTK (44), Diatomaceous earth (292), MT-10 (30) | 100 | — | 1,500 | 600 | — | — | — | Diatomaceous earth (58) | 2.2 |
| Example B6 | 400 | — | — | — | — | 200 | Dec-Gly (32), P3Na (10), FTK (44), Diatomaceous earth (292), MT-10 (30) | 100 | — | 1,500 | — | 600 | — | — | Diatomaceous earth (58) | 2.2 |
| Example B7 | 400 | — | — | — | 200 | — | Dec-Gly (32), P3Na (10), FTK (44), Diatomaceous earth (292), MT-10 (30) | 100 | — | 1,500 | — | 600 | — | — | Diatomaceous earth (58) | 2.2 |
| Example B8 | 400 | — | — | — | — | 200 | Dec-Gly (32), P3Na (10), FTK (44), Diatomaceous earth (292), MT-10 (30) | — | 100 | 1,500 | — | 600 | — | — | Diatomaceous earth (58) | 2.2 |
| Example B9 | — | 400 | — | — | — | 200 | Dec-Gly (32), P3Na (10), FTK (44), Diatomaceous earth (292), MT-10 (30) | 100 | — | 1,500 | — | 600 | — | — | Diatomaceous earth (58) | 2.2 |
| Example B10 | 300 | 100 | — | — | — | 200 | Dec-Gly (32), P3Na (10), FTK (44), Diatomaceous earth (292), MT-10 (30) | 100 | — | 1,500 | — | 600 | — | — | Diatomaceous earth (58) | 2.2 |
| Example B11 | 300 | 100 | 40 | 60 | — | 200 | Dec-Gly (32), P3Na (10), FTK (44), Diatomaceous earth (292), MT-10 (30) | 100 | — | 1,500 | — | 600 | — | — | Diatomaceous earth (58) | 2.0 |
| Example B12 | 300 | 100 | 40 | 60 | — | 200 | Dec-Gly (32), P3Na (10), FTK (44), Diatomaceous earth (292), MT-10 (30) | — | 100 | 1,500 | — | 600 | — | — | Diatomaceous earth (58) | 2.0 |

TABLE 9

| | Alginate impression material composition/parts by mass Curing material | | | | | | |
|---|---|---|---|---|---|---|---|
| | Gelling reaction agent | | | | Poorly water-soluble organic solvent Liquid | | |
| | Anhydrous gypsum | Dihydrated gypsum | ZnO | MgO | HeX | paraffin | Others |
| Example B13 | 500 | 400 | 50 | 50 | — | 200 | Dec-Gly (50), P3Na (10), FTK (44), Diatomaceous earth (292), MT-10 (30) |
| Example B14 | 100 | — | — | — | — | 100 | Dec-Gly (20), P3Na (10), FTK (44), Diatomaceous earth (292), MT-10 (30) |
| Example B15 | 1,500 | 500 | — | — | — | 200 | Dec-Gly (50), P3Na (10), FTK (44), MT-10 (30) |
| Example B16 | 10 | — | — | — | — | 20 | Dec-Gly (10), P3Na (10), FTK (44), Diatomaceous earth (450), MT-10 (30) |
| Example B17 | 300 | 100 | 40 | 60 | — | 200 | Dec-Gly (32), P3Na (10), FTK (44), Diatomaceous earth (292), MT-10 (30) |
| Example B18 | 300 | 100 | 40 | 60 | — | 200 | Dec-Gly (32), P3Na (10), FTK (44), Diatomaceous earth (292), MT-10 (30) |

| | Alginate impression material composition/parts by mass Base material | | | | | | | | Base material/curing material mixing ratio |
|---|---|---|---|---|---|---|---|---|---|
| | Alginic acid salt | | Water Distilled | Non-reducing sugar | | | | | |
| | ARK | ARNa | water | Sucrose | Trehalose | Cdex α | Cdex β | Others | |
| Example B13 | 100 | — | 1,500 | — | 600 | — | — | Diatomaceous earth (58) | 1.4 |
| Example B14 | 100 | — | 1,500 | — | 600 | — | — | Diatomaceous earth (58) | 3.8 |
| Example B15 | 100 | — | 1,500 | — | 600 | — | — | Diatomaceous earth (350) | 1.1 |
| Example B16 | 100 | — | 1,500 | — | 600 | — | — | Diatomaceous earth (58) | 3.9 |
| Example B17 | 100 | — | 2,000 | — | 600 | — | — | Diatomaceous earth (58) | 2.5 |
| Example B18 | 100 | — | 500 | — | 600 | — | — | Diatomaceous earth (58) | 1.1 |

TABLE 10

| | Alginate impression material composition/parts by mass | | | | | | | |
|---|---|---|---|---|---|---|---|---|
| | Curing material | | | | | | Base material Alginic acid salt | |
| | Gelling reaction agent | | | | Poorly water-soluble organic solvent | | | |
| | Anhydrous gypsum | Dihydrated gypsum | ZnO | MgO | Liquid paraffin | Others | ARK | ARNa |
| Example B19 | 300 | 100 | 40 | 60 | 200 | Dec-Gly (32), P3Na (10), PAA (22), FTK (44), Diatomaceous earth (380), MT-10 (30) | 100 | — |
| Example B20 | 300 | 100 | 40 | 60 | 200 | Dec-Gly (32), P3Na (10), PAA (22), FTK (44), Diatomaceous earth (10), MT-10 (30) | 100 | — |
| Example B21 | 300 | 100 | 40 | 60 | 200 | Dec-Gly (32), P3Na (10), PAA (22), FTK (44), Diatomaceous earth (292), MT-10 (30) | 100 | — |
| Example B22 | 300 | 100 | 40 | 60 | 200 | Dec-Gly (32), P3Na (10), PAA (22), FTK (44), Diatomaceous earth (292), MT-10 (30) | 100 | — |
| Example B23 | 300 | 100 | 40 | 60 | 200 | Dec-Gly (32), P3Na (10), PAA (22), FTK (44), Diatomaceous earth (292), MT-10 (30) | 100 | — |
| Example B24 | 300 | 100 | 40 | 60 | 200 | Dec-Gly (32), P3Na (10), PAA (22), FTK (44), Diatomaceous earth (292), MT-10 (30) | 100 | — |
| Example B25 | 300 | 100 | 40 | 60 | 200 | Dec-Gly (32), P3Na (10), PAA (22), FTK (44), Diatomaceous earth (292), MT-10 (30) | 100 | — |
| Example B26 | 300 | 100 | 40 | 60 | 200 | Dec-Gly (32), P3Na (10), PAA (22), FTK (44), Diatomaceous earth (470), MT-10 (30) | 100 | — |

| | Alginate impression material composition/parts by mass | | | | | | Base material/curing material mix ratio |
|---|---|---|---|---|---|---|---|
| | Base material | | | | | | |
| | Water Distilled water | Non-Reducing sugar | | | | Others | |
| | | Sucrose | Trehalose | Cdex α | Cdex β | | |
| Example B19 | 4,000 | — | 600 | — | — | Diatomaceous earth (58) | 3.91 |
| Example B20 | 100 | — | 600 | — | — | Diatomaceous earth (58) | 1.01 |
| Example B21 | 1,500 | — | 100 | — | — | Diatomaceous earth (58) | 1.56 |
| Example B22 | 2,000 | — | 200 | — | — | Diatomaceous earth (58) | 2.09 |
| Example B23 | 2,000 | — | 400 | — | — | Diatomaceous earth (58) | 2.26 |
| Example B24 | 2,000 | — | 1,200 | — | — | Diatomaceous earth (58) | 2.97 |
| Example B25 | 2,000 | — | 1,500 | — | — | Diatomaceous earth (58) | 3.24 |
| Example B26 | 3,000 | — | 2,000 | — | — | Diatomaceous earth (58) | 3.94 |

TABLE 11

| | Alginate impression material composition/parts by mass Curing material | | | | | |
|---|---|---|---|---|---|---|
| | Gelling reaction agent | | | | Poorly water-soluble organic solvent | |
| | Anhydrous gypsum | Dihydrated gypsum | ZnO | MgO | Liquid paraffin | Others |
| Comparative Example B1 | 400 | — | — | — | 200 | — |
| Comparative Example B2 | 300 | 100 | 40 | 60 | 200 | — |
| Comparative Example B3 | 300 | 100 | 40 | 60 | 200 | Dec-Gly (32), P3Na (10), PAA (22), FTK (44), Diatomaceous earth (292), MT-10 (30) |
| Example B27 | 300 | 100 | 40 | 60 | 200 | Dec-Gly (32), P3Na (10), PAA (22), FTK (44), Diatomaceous earth (292), MT-10 (30) |
| Example B28 | 300 | 100 | 40 | 60 | 200 | Dec-Gly (32), P3Na (10), PAA (22), FTK (44), Diatomaceous earth (470), MT-10 (30) |
| Example B29 | 300 | 100 | 40 | 60 | 200 | Dec-Gly (32), P3Na (10), PAA (22), FTK (44), Diatomaceous earth (292), MT-10 (30) |
| Comparative Example B4 | 300 | 100 | 40 | 60 | 200 | Dec-Gly (32), P3Na (10), PAA (22), FTK (44), Diatomaceous earth (292), MT-10 (30) |

| | Alginate impression material composition/parts by mass Base material | | | | | | Base material/ curing material mixing ratio |
|---|---|---|---|---|---|---|---|
| | Alginic acid salt | Water Distilled | Non-reducing sugar | Reducing sugar | | | |
| | ARK | water | Trehalose | Glucose | Lactose | Others | |
| Comparative Example B1 | 100 | 1,500 | — | — | — | — | 2.67 |
| Comparative Example B2 | 100 | 1,500 | — | — | — | — | 2.29 |
| Comparative Example B3 | 100 | 1,500 | — | — | — | Diatomaceous earth (58) | 1.47 |
| Example B27 | 100 | 1,500 | 50 | — | — | Diatomaceous earth (58) | 1.51 |
| Example B28 | 100 | 3,000 | 2,200 | — | — | Diatomaceous earth (58) | 4.10 |
| Example B29 | 100 | 1,500 | 50 | 550 | — | Diatomaceous earth (58) | 2.00 |
| Comparative Example B4 | 100 | 1,500 | — | — | 600 | Diatomaceous earth (58) | 2.00 |

TABLE 12

|  | Surface lubrication property | | Compatible deformation μm | | | |
| --- | --- | --- | --- | --- | --- | --- |
|  | Immediately after | After 3 days | Immediately after | After 5 hours | After 1 day | After 3 days |
| Example B1 | A | B | 350 | 510 | 620 | 890 |
| Example B2 | A | B | 345 | 390 | 440 | 605 |
| Example B3 | A | B | 355 | 515 | 610 | 885 |
| Example B4 | A | B | 350 | 525 | 623 | 890 |
| Example B5 | A | B | 220 | 360 | 425 | 640 |
| Example B6 | A | A | 215 | 225 | 310 | 435 |
| Example B7 | A | A | 225 | 235 | 312 | 442 |
| Example B8 | A | A | 220 | 232 | 323 | 440 |
| Example B9 | A | A | 235 | 246 | 319 | 462 |
| Example B10 | A | A | 190 | 210 | 314 | 424 |
| Example B11 | A | A | 110 | 120 | 220 | 340 |
| Example B12 | A | A | 112 | 118 | 219 | 341 |
| Example B13 | A | A | 115 | 126 | 216 | 344 |
| Example B14 | A | A | 122 | 130 | 210 | 338 |
| Example B15 | A | B | 242 | 255 | 345 | 456 |
| Example B16 | A | B | 262 | 289 | 397 | 502 |
| Example B17 | A | A | 124 | 129 | 208 | 335 |
| Example B18 | A | A | 130 | 134 | 212 | 342 |
| Example B19 | A | A | 241 | 251 | 310 | 458 |
| Example B20 | A | A | 256 | 269 | 309 | 472 |
| Example B21 | A | A | 198 | 214 | 312 | 425 |
| Example B22 | A | A | 154 | 169 | 274 | 389 |
| Example B23 | A | A | 116 | 123 | 222 | 349 |
| Example B24 | A | A | 111 | 128 | 229 | 342 |
| Example B25 | A | A | 174 | 192 | 297 | 402 |
| Example B26 | A | A | 229 | 241 | 329 | 458 |

TABLE 13

|  | Surface lubrication property | | Compatible deformation μm | | |
| --- | --- | --- | --- | --- | --- |
|  | Immediately after | After 1 hour | Immediately after | After 30 minutes | After 1 hour |
| Comparative Example B1 | B | D | 352 | 1,510 | 2,425 |
| Comparative Example B2 | B | D | 342 | 1,490 | 2,400 |
| Comparative Example B3 | B | D | 220 | 1,200 | 2,250 |
| Example B27 | B | D | 215 | 1,150 | 2,190 |
| Example B28 | B | D | 560 | 1,190 | 2,050 |
| Example B29 | B | D | 240 | 1,235 | 2,322 |
| Comparative Example B4 | B | D | 235 | 1,215 | 2,290 |

In any of Example B1 to Example B26, the water retentivity was satisfactory, and the cured product was suppressed from being dried even when left to stand for a long period of time after impression taking, resulting in satisfactory impression accuracy. On the other hand, in any of Comparative Example B1 to Comparative Example B3 having no non-reducing sugar blended therein, the cured product was dried when left to stand for about 30 minutes after impression taking, resulting in a remarkable decrease in impression accuracy.

In Example B27, the blending amount of the non-reducing sugar was less than 1 part by weight with respect to 1 part by weight of the alginic acid. In Example B27, the water retentivity tended to slightly improve but was still insufficient. Hence, the cured product was dried when left to stand for about 30 minutes after impression taking, resulting in a remarkable decrease in impression accuracy. Further, in Example B28, the blending amount of the non-reducing sugar was more than 20 parts by weight with respect to 1 part by weight of the alginic acid. In Example B28, the impression accuracy at the initial stage (immediately after impression taking) remarkably decreased, the effect on the water retentivity was also insufficient, and the cured product was dried when left to stand for about 30 minutes after impression taking, resulting in a decrease in impression accuracy.

In each of Example B29 and Comparative Example B4, the reducing sugar was used in place of the non-reducing sugar. In each of Example B29 and Comparative Example B4, the water retentivity tended to slightly improve but was still insufficient. Hence, the cured product was dried when left to stand for about 30 minutes after impression taking, resulting in a remarkable decrease in impression accuracy.

<<Evaluation on Viscosity Remaining Rate>>

Example B30

10 g of ARK as an alginic acid, 150 g of distilled water as water, and 60 g of sucrose as a non-reducing sugar were weighed and kneaded together through the use of a small kneader (I-ko mixer manufactured by I-ko Industrial Co., Ltd.) for 1 hour to prepare a base material paste.

Example B31 to Example B33 and Comparative Example B5 to Comparative Example B8

Base material pastes were each prepared in the same manner as in Example B30 except that the composition of the base material paste was changed to one shown in Table 14.

(Evaluation Results)

Table 14 shows the evaluation results of the composition and base material paste viscosity remaining rate of each of the base material pastes of Examples B30 to B33 and Comparative Examples B5 to B8.

TABLE 14

| | | Alginate impression material base material paste composition/parts by mass | | | | | | Base material paste viscosity remaining rate/% | | |
| --- | --- | --- | --- | --- | --- | --- | --- | --- | --- | --- |
| | | Alginic acid salt (A) | | Water (C) | Non-reducing sugar (D) | | | | | |
| | Remark | ARK | ARNa | Distilled water | Sucrose | Trehalose | Others | Initial | After 1 week | After 3 weeks |
| Example B30 | Base material paste used in Example B1 | 100 | — | 1,500 | 600 | — | — | 100 | 84.2 | 76.2 |
| Example B31 | Base material paste used in Example B2 | 100 | — | 1,500 | — | 600 | — | 100 | 91.4 | 81.2 |
| Example B32 | Base material paste used in Example B8 | — | 100 | 1,500 | — | 600 | Diatomaceous earth (58) | 100 | 97.5 | 88.9 |
| Example B33 | Base material paste used in Example B6 | 100 | — | 1,500 | — | 600 | Diatomaceous earth (58) | 100 | 98.2 | 89.9 |

TABLE 14-continued

| | | Alginate impression material base material paste composition/parts by mass | | | | | | Base material paste viscosity remaining rate/% | | |
| | | Alginic acid salt (A) | | Water (C) | Non-reducing sugar (D) | | | | | |
| | Remark | ARK | ARNa | Distilled water | Sucrose | Trehalose | Others | Initial | After 1 week | After 3 weeks |
|---|---|---|---|---|---|---|---|---|---|---|
| Comparative Exampe B5 | — | 100 | — | 1,500 | — | — | — | 100 | 58.2 | 38.2 |
| Comparative Exampe B6 | — | — | 100 | 1,500 | — | — | — | 100 | 67.1 | 44.2 |
| Comparative Exampe B7 | — | 100 | — | 1,500 | — | — | Glucose (600) | 100 | 57.1 | 32.2 |
| Comparative Exampe B8 | — | 100 | — | 1,500 | — | — | Diatomaceous earth (58) | 100 | 60.1 | 35.9 |

In each of Example B30 to Example B33, the blending amount of the non-reducing sugar is 6 parts by weight with respect to 1 part by weight of the alginic acid. In any of Example B30 to Example B33, the viscosity remaining rate of the base material paste is 70% or more, indicating that a time-dependent decrease in viscosity is suppressed to a large extent. On the other hand, in each of Comparative Example B5 to Comparative Example B8, a base material paste containing an alginic acid and water as main components is not blended with any non-reducing sugar. In any of Comparative Example B5 to Comparative Example B8, a time-dependent decrease in viscosity is found to be remarkable as compared to Example B30 to Example B33.

The invention claimed is:

1. A dental alginate impression material, comprising a cured product which is obtained by mixing and kneading a base material with a curing material, wherein:
   the base material comprising an alginic acid-containing aqueous composition comprising:
      alginic acid or a derivative thereof (A);
      water (B); and
      a non-reducing sugar (C); and
   the curing material,
wherein:
   the base material is pasty; and
   the curing material comprises a pasty curing material comprising a gelling reaction agent and a poorly water-soluble organic solvent.

2. A dental alginate impression material according to claim 1, wherein
   a content of the non-reducing sugar (C) falls within a range of 1 part by weight to 20 parts by weight with respect to 1 part by mass of the alginic acid or the derivative thereof (A).

3. A dental alginate impression material according to claim 1, wherein
   the non-reducing sugar (C) comprises 2 to 10 monosaccharide molecules bonded via a glycosidic bond.

4. A dental alginate impression material according to claim 1, wherein
   the non-reducing sugar (C) comprises a disaccharide.

5. A dental alginate impression material according to claim 1, wherein
   the non-reducing sugar (C) comprises trehalose.

6. A method of taking a dental impression comprising:
   providing a pasty base material comprising an alginic acid-containing aqueous composition comprising alginic acid or a derivative thereof (A), water (B), and a non-reducing sugar (C);
   providing a pasty curing material comprising a gelling reaction agent and a poorly water-soluble organic solvent;
   preparing a kneaded product by mixing and kneading the pasty base material with the pasty curing material;
   mounting the kneaded product on a tray;
   pressing the tray against a dental target to obtain the dental impression on the kneaded product.

* * * * *